(12) United States Patent
Neef et al.

(10) Patent No.: US 9,063,099 B2
(45) Date of Patent: Jun. 23, 2015

(54) SYSTEM FOR HANDLING SLIDES HAVING A LINEAR TRANSPORT MECHANISM FOR TRANSPORTING THE RACKS

(75) Inventors: Bernhard Neef, Nussloch (DE); Simon Keimer, Leimen (DE); Karl-Heinz Westerhoff, Eppingen (DE)

(73) Assignee: LEICA BIOSYSTEMS NUSSLOCH GMBH, Nussloch (DE)

( * ) Notice: Subject to any disclaimer, the term of this patent is extended or adjusted under 35 U.S.C. 154(b) by 554 days.

(21) Appl. No.: 13/469,621

(22) Filed: May 11, 2012

(65) Prior Publication Data

US 2012/0290127 A1    Nov. 15, 2012

(30) Foreign Application Priority Data

May 13, 2011    (DE) .......................... 10 2011 050 343

(51) Int. Cl.
G06F 7/00    (2006.01)
G01N 35/00   (2006.01)
G01N 35/02   (2006.01)

(52) U.S. Cl.
CPC .................... *G01N 35/00029* (2013.01); *G01N 2035/00079* (2013.01); *G01N 2035/00138* (2013.01); *G01N 35/026* (2013.01)

(58) Field of Classification Search
None
See application file for complete search history.

(56) References Cited

U.S. PATENT DOCUMENTS

| 7,767,148 B2 * | 8/2010 | Takahashi et al. ............... 422/65 |
| 2003/0047567 A1 | 3/2003 | Plank et al. |
| 2012/0163630 A1 * | 6/2012 | Yano et al. ..................... 381/107 |
| 2012/0163680 A1 * | 6/2012 | Lefebvre ....................... 382/128 |

FOREIGN PATENT DOCUMENTS

| EP | 2239554 A1 | 10/2010 |
| GB | 2485871 A | 5/2012 |
| WO | 03/089140 A1 | 10/2003 |

OTHER PUBLICATIONS

United Kingdom Intellectual Property Office, Combined Search and Examination Report issued Jul. 16, 2012 in counterpart British Application No. GB1205849.1.

* cited by examiner

*Primary Examiner* — Yolanda Cumbess
(74) *Attorney, Agent, or Firm* — Hodgson Russ LLP

(57) ABSTRACT

The present invention relates to a system (10, 100) for handling slides, including an input compartment (14) for inputting racks (16) and the slides held therein, and a coverslipper module (30, 32) for coverslipping slides. The system (10, 100) further includes an output compartment (22) for outputting racks (16), a transport unit (20) for transporting the racks (16), and a control unit (52) for controlling the transport unit (20). The transport unit (20) is designed to be capable of transporting the racks (16) between the input compartment (14), the coverslipper module (30, 32) and the output compartment (22).

14 Claims, 7 Drawing Sheets

SYSTEM FOR HANDLING SLIDES HAVING A LINEAR TRANSPORT MECHANISM FOR TRANSPORTING THE RACKS

CROSS REFERENCE TO RELATED APPLICATIONS

This application claims priority of German patent application number 10 2011 050 343.9 filed May 13, 2011, the entire disclosure of which is incorporated by reference herein.

FIELD OF THE INVENTION

The present invention relates to a system for handling slides, including an input compartment for inputting racks and the slides held therein, and a coverslipper module for coverslipping thin sections on the slides with a mounting medium and a cover slip. The system further includes an output compartment for outputting racks, a transport unit for transporting the racks, and a control unit for controlling this transport unit.

BACKGROUND OF THE INVENTION

In histology, thin sections obtained from tissue samples are placed on sample carriers referred to as slides. In order to prepare the slides for microscopy, the thin sections placed on the slides are typically treated, in particular dehydrated or stained. To protect the thin sections, a cover slip is placed on top. Prior to placement of the cover slip, a mounting medium is applied via which the cover slip adheres to the slide. After checking the coverslipping quality, the slides carrying the coverslipped thin sections are transferred to a microscope for further examination of the thin sections.

In known coverslipper modules, a first transport unit is provided which transports the racks placed in the input compartment from this input compartment to the coverslipper module. After the slides are coverslipped, a second transport unit different from the first transport unit transports the slides further to a quality control module which checks the coverslipping quality. Subsequently, the slides are transported by a third transport unit from the quality control module to an output compartment. Such known automated coverslippers are problematic because they have a plurality of transport units and each of the plurality of transport units is intended for only one transport within the coverslipper, which results in a complex, involved and thus expensive design. Furthermore, the susceptibility to faults increases with the number of transport units.

SUMMARY OF THE INVENTION

It is an object of the present invention to provide a system for handling slides that is simple and compact in design.

This object is achieved by a system having the features of described herein. Advantageous embodiments of the present invention are described in the present specification.

In accordance with the present invention, the transport unit is designed to be capable of transporting the racks between the input compartment, the coverslipper module and the output compartment. Thus, it is sufficient to provide one single transport unit capable of carrying out all rack transports within the system. This results in a particularly cost-effective and simple design.

Preferably, the system has a drying unit capable of removing the moisture of the mounting medium from the coverslipped slides. Such a drying unit causes the mounting medium to dry faster, preventing the cover slips from being displaced, and thus preventing damage to the thin sections and injury to a user. The transport unit is designed to also be capable of transferring and/or removing the racks to/from the drying unit. This eliminates the need for a separate transport unit for transports to the drying unit and from the drying unit to the output compartment.

In particular, the system has a first module-receiving area for receiving a module for handling slides and/or at least a second module-receiving area for receiving a further module for handling slides. In the first module-receiving area there is disposed, in particular, the coverslipper module as the module for handling slides. The transport unit is designed to be capable of transferring and/or removing racks to/from a module disposed in the first module-receiving area and/or to/from a module disposed in the second module receiving area. By providing two module-receiving areas in which modules for handling slides may be placed, the configuration of the system can be easily adapted to individual customer requirements. In spite of the great flexibility in the configuration of the system, only one transport unit is needed because this transport unit can transfer and remove racks to and from both module-receiving areas, so that the module receiving areas can be equipped with the modules as desired and all necessary transport operations can be easily carried out using only one transport unit.

In the second module-receiving area there is disposed, as the module for handling slides, in particular a quality control module for checking the quality of thin sections placed on the slides and/or the coverslipping quality. In this case, the transport unit transports the racks, in particular, from the input compartment first to the coverslipper module disposed in the first module-receiving area and, after coverslipping the slides of the rack, from this coverslipper module to the quality control module received in the second module-receiving area. Subsequently, the racks are transferred from this quality control module to the drying unit and, after drying, further to the output compartment.

In a particularly preferred embodiment of the present invention, a coverslipper module for coverslipping slides is provided in each of the two module-receiving areas, thereby increasing the throughput; i.e., the number of slides that can be coverslipped per unit time. In particular, the two coverslipper modules may use different mounting media, allowing slides to be coverslipped with different mounting media without having to modify the configuration of the system, and in particular without having to clean the system for this purpose. Since the transport unit is capable of transporting the racks as desired between the various units of the system, the racks can be transferred to and removed from the first module-receiving area and a second module-receiving area by one single transport unit.

The quality control module includes, in particular, a camera which captures at least one image showing at least the portion of the slide where the thin section is located. The control unit executes at least one stored image-processing algorithm. In this process, the staining quality of the thin section, mechanical damage to the thin section and/or to the cover slip, the relative position of the thin section on the slide and/or air inclusions between the slide and the cover slip are detected by the control unit based on the captured image.

Further, it is advantageous if the transport unit is designed in such a way that the racks can be transported directly between the input compartment, the coverslipper module, the first module-receiving area, the second module-receiving area, the drying unit, and the output compartment without having to be previously transferred to any of the other units or areas. This allows the racks to be transported between the various units or areas as desired, which allows for great flexibility. In particular, in the case of units operating in parallel, this eliminates the need to synchronize these units to each other.

The system includes, in the input compartment, in particular a reader unit for reading information from an information carrier attached to the inserted rack. The control unit controls the transport unit based on this information. In particular, the control unit determines, based on the information read, which of the modules in the module-receiving areas the rack is to be transported to and, possibly, the order in which the rack is to be successively transferred to the various module-receiving areas. The information read includes, in particular, information on which mounting medium is to be used. Based on the mounting medium to be used, the control unit controls the transport unit to transfer the rack to the coverslipper module that uses the right mounting medium. The information carrier may, for example, be an RFID chip and/or a bar code.

The system is, in particular, designed with two levels, the first level accommodating the input compartment, the reader unit, the drying unit and/or the output compartment, and the second level accommodating the module-receiving areas. When the system is in its normal operating orientation, the second level is located in particular above the first level. The transport unit is designed to be capable of transporting racks between the two levels.

In a particularly preferred embodiment, the transport unit includes a first linear guide member oriented in a first direction and a first carriage mounted on the first guide member such that it is movable in the first direction and in a direction opposite to the first direction. The first carriage has disposed thereon a second linear guide member which is oriented in a second direction orthogonal to the first direction and which is fixedly connected to the first carriage. Thus, when the carriage moves in the first direction or in a direction opposite to the first direction, the second guide member is correspondingly carried along with the carriage. The second guide member has mounted thereon a second carriage which is movable in the second direction and in a direction opposite to the second direction. The transport unit further includes a gripper for holding at least one rack while this rack is being transported. The gripper is movable by the first carriage in the first direction and in a direction opposite to the first direction, and by the second carriage in the second direction and in a direction opposite to the second direction. Thus, the linear guides formed by the guide members and the carriages enable the racks to be transported as desired within the plane defined by the two linear guide members. Consequently, no specific transport path is defined as the only path along which the racks can be transported. Instead, transport can be along any desired path within these transport planes, so that, by simple means, a transport unit is created which is capable of transferring and removing the racks directly to/from all units and areas of the system.

The system further includes in particular a first drive unit which drives a first belt securely connected to the first carriage. The first carriage is moved along the first guide member by this belt. Moreover, the system may include a second drive unit which moves the second carriage along the second guide member by means of a second belt securely connected to this second guide member. Each of the two drive units is provided in particular by an electric motor. In an alternative embodiment, only one drive unit may be provided and used for moving both carriages along the respective guide members.

The first guide member is mounted, in particular, on a wall of a housing of the system. This results in a design which is particularly cost-effective, yet allows the racks to be transported as desired within the system. The housing wall is, in particular, a rear wall; i.e., the wall opposite the operator side where a user operates the system. Thus, the modules are easily accessible by the user because the transport unit transfers the racks to the modules from behind, as seen from the perspective of the user, so that the transport unit does not obstruct access to the modules.

The first guide member has, in particular, a length of 0.8 to 0.9 times the width of the housing of the system. Thus, the racks can be transported across nearly the entire width of the housing by means of the transport unit. Similarly, the length of the second guide member is, in particular, between 0.5 and 0.95 times, preferably between 0.6 and 0.7 times the height of the housing of the system. As a result, the racks can also be transported across nearly the entire height within the system, which overall provides a maximum possible transport range within which the racks may be moved by means of the transport unit.

The height of the system or housing is understood to be in particular the vertical dimension of the housing in the normal operating orientation of the system. The width refers in particular to the horizontal dimension of the housing orthogonal to the height, as seen from the perspective of a user. Accordingly, the depth refers to the dimension of the housing orthogonal to the width and height and pointing away from the user.

In a particularly preferred embodiment, a third linear guide member is provided which is fixedly connected to the second carriage. The third guide member is oriented in a third direction which is orthogonal to the first direction and orthogonal to the second direction. The gripper is mounted on the third guide member in such a way that it is movable in the third direction or in a direction opposite thereto. In particular, a third carriage is provided which is mounted on the third guide member such that it is movable in the third direction and in a direction opposite to the third direction and to which is attached the gripper. This allows the racks to be transported in three dimensions within a transport space defined by the three guide members. Since the transport unit is constituted of three linear guide members oriented orthogonal to one another, the racks are capable of being transported along any desired transport path within the transport space, so that the racks can be transported as desired between the various units and modules of the system. In particular, the three guide members are oriented relative to each other in a manner similar to a Cartesian coordinate system.

The system further includes in particular a third drive unit which drives a third belt securely connected to the gripper in order to move the gripper along the third guide member. This drive unit is also in particular provided by an electric motor.

The first guide member, the second guide member and/or the third guide member may each be configured as a shaft or as a rail. The shaft-type design is particularly cost-effective to manufacture, while the rail-type design allows for precise guidance without any support means being needed for the carriage. The rails are configured in particular as profiled rails. In a particularly preferred embodiment, the first guide member is configured as a shaft, while the second and third guide members are each configured as a rail.

The gripper includes in particular a first holding member and a second holding member for holding the rack to be transported. The two holding members are spaced apart by a first predetermined distance in a first position and by a second predetermined distance in a second position. When spaced apart by the first distance, the holding members hold a rack located therebetween, whereas when they are spaced apart by the second distance, the rack located therebetween is no longer held by the holding members. The gripper further includes at least one elastic member, such as a spring, which holds the holding members in the first position, as well as an adjusting element which moves the two holding members from the first to the second position against the restoring force of the elastic member. The adjusting unit is in particular in the form of an additional drive unit. The preloading in the first position ensures that the racks are securely held and prevented from accidentally falling out of the gripper, even in the event of a power failure. In an alternative embodiment of the present invention, the holding members may also be preloaded in the second position.

The gripper includes, in particular, at least one engagement element which engages into a complementary engagement element of a rack so as to hold the rack. Specifically, each holding member has one engagement element provided thereon which engages into an engagement element of the rack when the holding members are in the first position. This ensures that the racks are securely held during transport.

BRIEF DESCRIPTION OF THE DRAWING VIEWS

Further features and advantages of the present invention will become apparent from the following description of exemplary embodiments thereof, taken in conjunction with the accompanying drawings, in which.

DETAILED DESCRIPTION OF THE INVENTION

Figure 1:
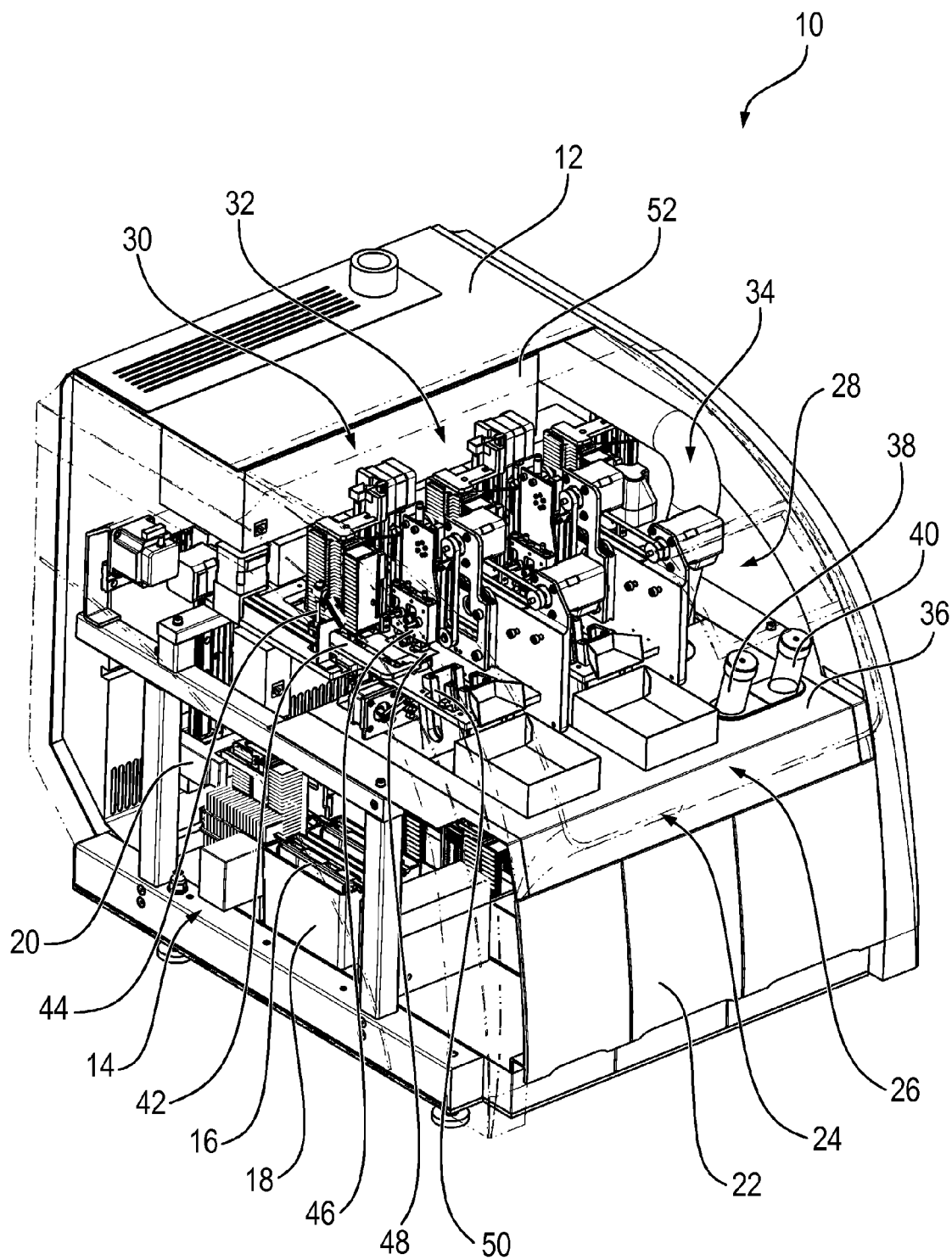
FIG. 1 is a schematic perspective view of an automated coverslipper according to a first embodiment.

FIG. 1 shows in schematic perspective form a system for handling slides according to a first embodiment in the form of a coverslipper 10. System 10 includes a housing 12 which is partially indicated by a dot-dash line in FIG. 1 so that the components located in and protected by housing 12 may be seen.

Coverslipper 10 includes an input compartment 14 via which racks 16 can be introduced into coverslipper 10. Located in racks 16 are slides having thin sections placed thereon which are to be coverslipped by coverslipper 10.

The slides may be introduced both manually and mechanically. This allows for both a stand-alone mode of operation, in which coverslipper 10 is not connected to other systems, and for a workstation mode of operation. In the workstation mode of operation, coverslipper 10 is disposed in particular adjacent to an automated stainer, so that once the thin sections placed on the slides have been stained, the slides are automatically received into racks 16 and transferred from the stainer to coverslipper 10. The racks 16 introduced via input compartment 14 are received in containers filled with xylene and held therein until they are processed, one of said containers being denoted, by way of example, by reference numeral 18.

Coverslipper 10 further has a transport unit 20 which allows the racks to be transported within coverslipper 10 and which will be described in greater detail below in conjunction with FIGS. 2 through 6. This transport unit 20 is designed to be capable of carrying out all transport operations of racks 16 within coverslipper 10 that are necessary to coverslip the slides. In particular, this single transport unit 20 is able to perform all transport operations of racks 16, from the introduction via input compartment 14 to the output via an output compartment 22. This results in a particularly simple and cost-effective design and also reduces the susceptibility to faults.

Coverslipper 10 has three module-receiving areas 24 through 28 for receiving one module for handling slides each. In the exemplary embodiment shown in FIG. 1, each of the first module-receiving area 24 and the second module-receiving area 26 has disposed therein a coverslipper module 30, 32 for coverslipping thin sections placed on slides. Third module-receiving area 28 has a quality control module placed therein. Alternatively, two of the module-receiving areas 24 through 28 may accommodate quality control modules 34 therein while only one of the module-receiving areas 24 through 28 may have a coverslipper module 30, 32 placed therein. Alternatively, it is also possible to provide only one coverslipper module 30, 32 and one quality control module 34. Similarly, only one coverslipper module 30, 32 may be provided while the other two module-receiving areas 24 through 28 may not be equipped with a module 30 through 34.

Coverslipper 10 further includes two mounting medium reservoirs, which are not visible in FIG. 1. A first one of these mounting medium reservoirs is connected to first coverslipper module 30 while the second mounting medium reservoir is connected to second coverslipper module 32. The two mounting medium reservoirs can be filled with mounting media independently of each other via the two inlet ports 38, 40. The first mounting medium received in the first mounting medium reservoir is pumped to first coverslipper module 30, in particular by means of a first pump (not visible). Analogously, the second mounting medium received in the second mounting medium reservoir is pumped to second coverslipper module 32 by a second pump.

In the exemplary embodiment shown in FIG. 1, the two coverslipper modules 30, 32 are identical in design. Therefore, the explanations given below by way of example for first coverslipper module 30 apply analogously to second coverslipper module 32. In an alternative embodiment, the two coverslipper modules 30, 32 may be designed differently.

First coverslipper module 30 includes a removal unit 42 by means of which the slides in the rack 16 that has been introduced into first coverslipper module 30 are removed one after the other from this rack 16. Subsequently, a predetermined amount of the first mounting medium is applied to the slide in the region of the thin section using a hollow needle 44. Then, a suction cup device 46 removes a cover slip 48 from a coverslip container 50 and covers the thin section with this cover slip 48. After the slide is covered, it is transported back into rack 16 by removal unit 42. More specifically, the slide is transported into the same holding compartment in which it was held previously. Then, rack 16 is displaced to a position where removal unit 42 can remove another slide therefrom for coverslipping.

By providing two mounting medium reservoirs, the two coverslipper modules 30, 32 can be operated independently of each other; i.e., one coverslipper module 30, 32 can coverslip slides simultaneously with the other coverslipper module 30, 32. This makes it possible, in particular, to store two different mounting media in the two mounting medium reservoirs, so that, unlike the known coverslippers which have only one coverslipper module 30, 32, there is no need to change the mounting medium when different mounting media are required depending on the type of thin section.

Input compartment 14 includes a reader unit capable of reading information from an information carrier attached to rack 16, such as, for example, a bar code or an RFID chip. This information includes, in particular, information for uniquely identifying rack 16. Based on the information read from the information carrier, a control unit 52 of coverslipper 10 determines the mounting medium with which the slides received in this rack 16 are to be coverslipped. Accordingly, control unit 52 then controls transport unit 20 to transport rack 16 to the coverslipper module 30, 32 that contains the right mounting medium. Thus, the assignment of racks 16 to the two coverslipper modules 30, 32 operating in parallel can be accomplished automatically without having to make a manual selection. Control unit 52 has stored therein, in particular, a database in which the mounting medium to be used for a particular rack 16 is stored uniquely for each rack. Based on the information read, control unit 52 may uniquely identify rack 16, and thus read information from the database as to which mounting medium is to be used.

In an alternative embodiment, the information stored on the information carriers of racks 16 may already include the information as to which mounting medium is to be used. In this case, there is no need to store such a database in control unit 52.

Once all slides of a rack 16 received in one of coverslipper modules 30, 32 have been coverslipped, transport unit 20 removes this rack 16 from coverslipper module 30, 32 and transfers it to a drying unit, which is not visible in FIG. 1. The drying unit removes moisture from the mounting medium, so that the mounting medium dries up faster and the cover slip adheres securely to the slide and cannot be displaced during further handling of the slides. The drying unit includes, in particular, a drying chamber in which a plurality of racks 16 can be received at the same time and through which is passed a stream of air heated to a predetermined temperature by a heating element, so that the slides located in the air stream are reliably, quickly and gently dried.

After drying, transport unit 20 removes rack 16 from the drying unit and transfers it to quality control module 34, which is received in third module-receiving area 28. This quality control module 34 includes a camera which captures at least one image showing at least the coverslipped thin section of each slide. The coverslipping quality is determined based on this image. In particular, control unit 52 has image-processing algorithms stored therein, which are executed by the control unit and which make it possible to detect damage to the thin sections, cover slips and/or to the slides, air inclusions between the cover slip and the slide and/or improper staining of the thin sections. If quality control module 34 should detect that the coverslipping quality of a slide does not meet the specified minimum requirements, it outputs, in particular, information indicative of this condition to the user of coverslipper 10.

Once quality control module 34 has checked the coverslipping quality of all the slides received in rack 16, transport unit 20 transports rack 16 and the slides received back therein into output compartment 22, so that it can be removed by a user. Alternatively, removal can be performed automatically. Output compartment 22 is configured, in particular, in the manner of a drawer, which allows for easy removal of racks 16.

In order to enable racks 16 to be transported as desired between module-receiving areas 24 through 28 and the other units of coverslipper 10 when the various module-receiving areas 24 through 28 are equipped with different modules 30 through 34, transport unit 20 is designed to be capable of transporting racks 16 as desired between the various units and modules 30 through 34 of coverslipper 10 without having to transport the racks in a particular sequence between the units and modules 30 through 34. To this end, transport unit 20 is designed as a linear transport mechanism having three linear guides oriented orthogonal to one another, which allows racks 16 to be transported along any desired transport path within a defined transport space. To this end, transport unit 20 is, in particular, controlled by control unit 52.

Figure 2:
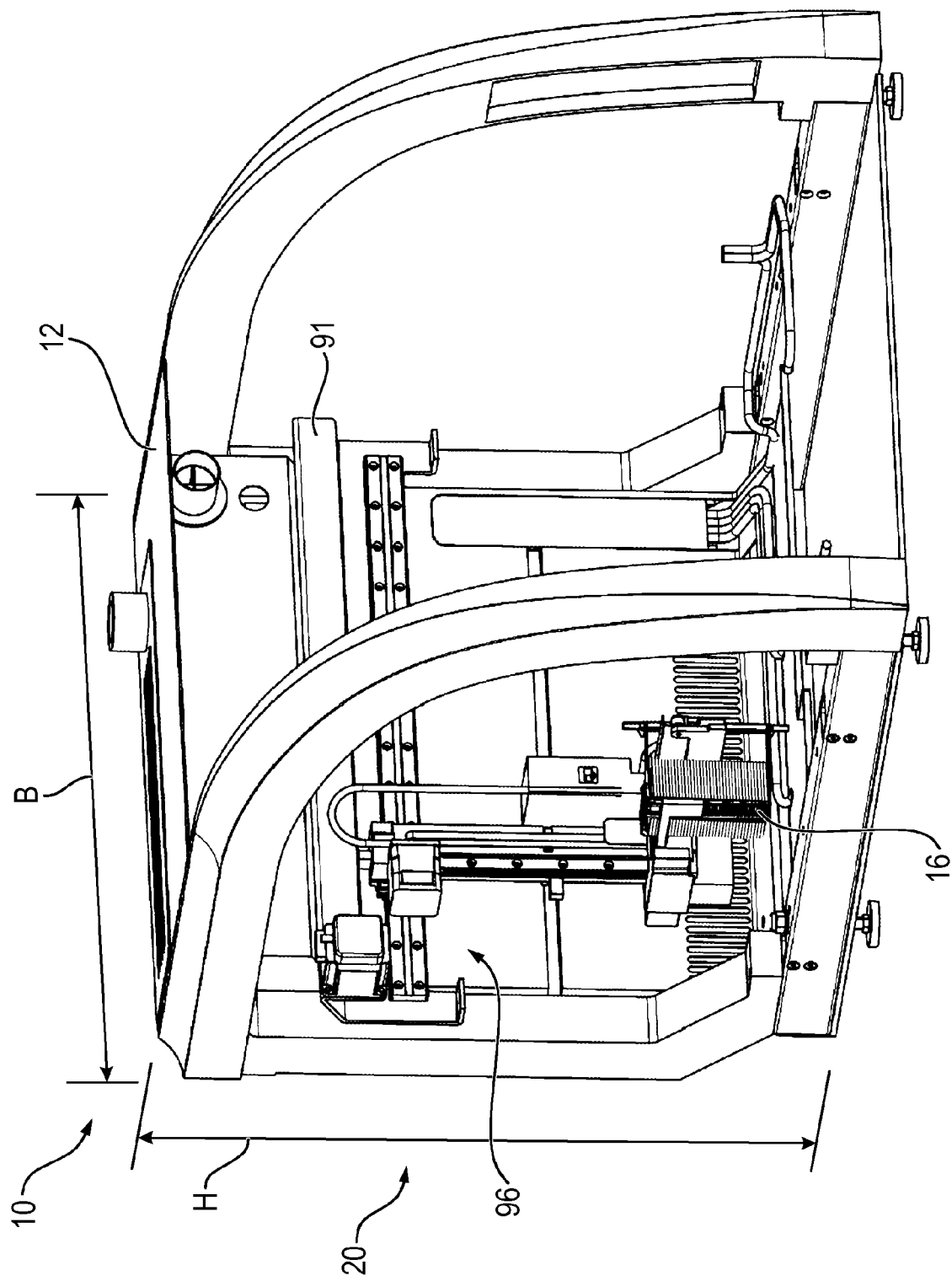
FIG. 2 is a view showing a portion of the system shown FIG. 1.
Figure 3:
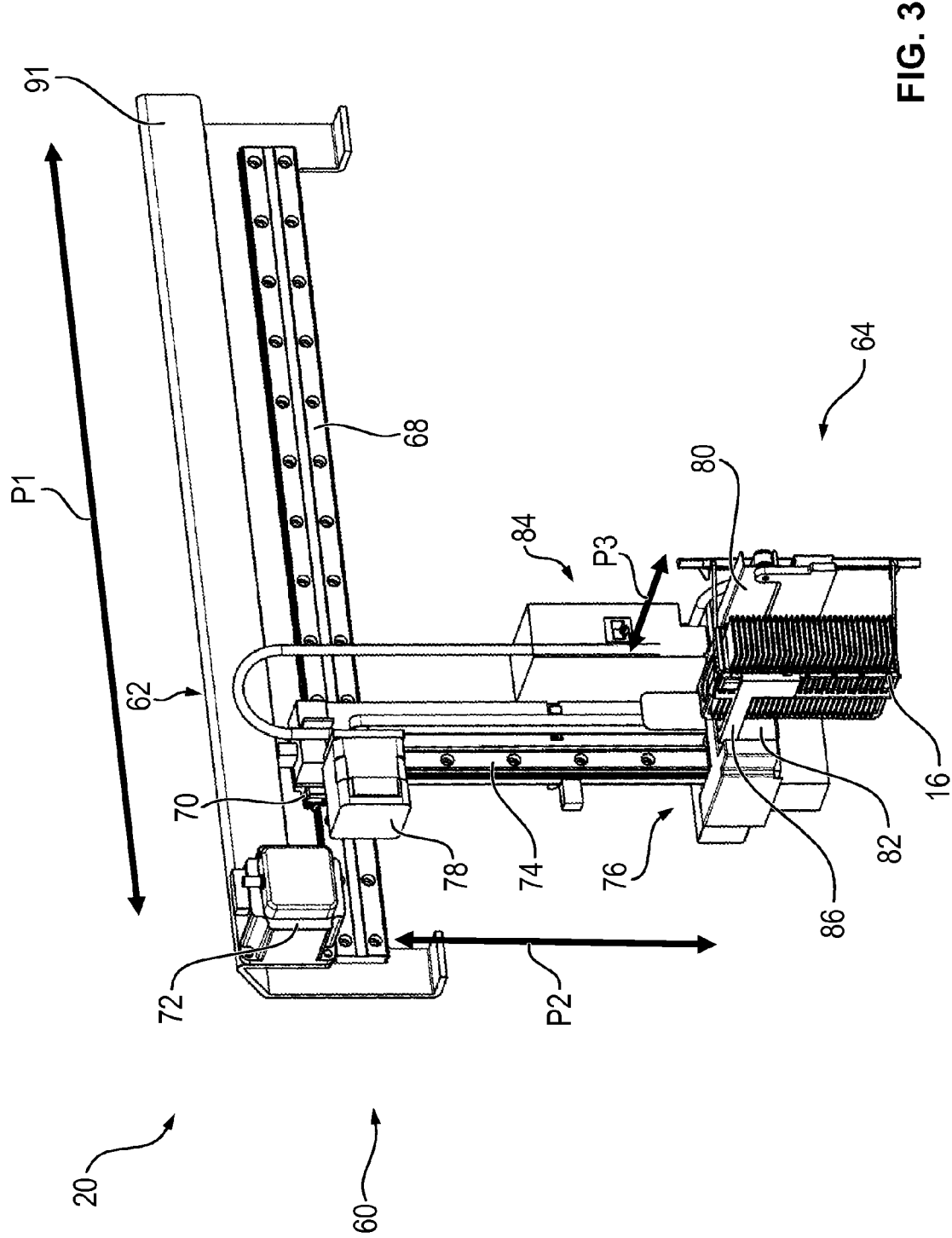
FIG. 3 is a schematic perspective view of a transport unit of the system shown in FIGS. 1 and 2.

FIG. 2 shows a portion of coverslipper 10 of FIG. 1 in a schematic perspective view, showing only part of housing 12 as well as transport unit 20 with a rack 16 held by it. FIG. 3 shows transport unit 20 in a schematic perspective view.

Transport unit 20 includes three linear guides 60 through 64 which are oriented orthogonal to one another, so that directions P1 through P3 are orthogonal to each other. This allows transport unit 20 to easily access any position within a three-dimensional space.

First linear guide 60 includes a first rail 68 and a carriage 70 which is mounted on this first rail 68 and movable along the rail 68 in the direction of double-headed arrow P1 by means of a first electric motor 72. To this end, carriage 70 is, in particular, securely connected to a belt capable of being driven by first motor 72. Alternatively, it is also possible to use a chain in place of a belt. The belt is not visible because it is covered by rail 68 or support unit 91, to which rail 68 is mounted.

Second linear guide 62 includes a second rail 74 which is fixedly connected to first carriage 70, so that when first carriage 70 moves in the direction of arrow P1, second rail 74 and all components mounted thereon are carried along with the first carriage. Second rail 74 has mounted thereon a second carriage 76 which is movable in the direction of double-headed arrow P2. To this end, carriage 76 is securely connected to a belt (not shown in FIG. 3) which is capable of being driven by a second electric motor 78.

A third rail 80 of third linear guide 64 is fixedly mounted to second carriage 76, so that when carriage 76 moves, said rail is carried along therewith. Third rail 80 has provided thereon a third carriage 82 which is movable by a third motor 84 in the direction of double-headed arrow P3. The movement of carriage 82 may in turn be accomplished, in particular, via a belt driven by a third electric motor 84.

Figure 4:
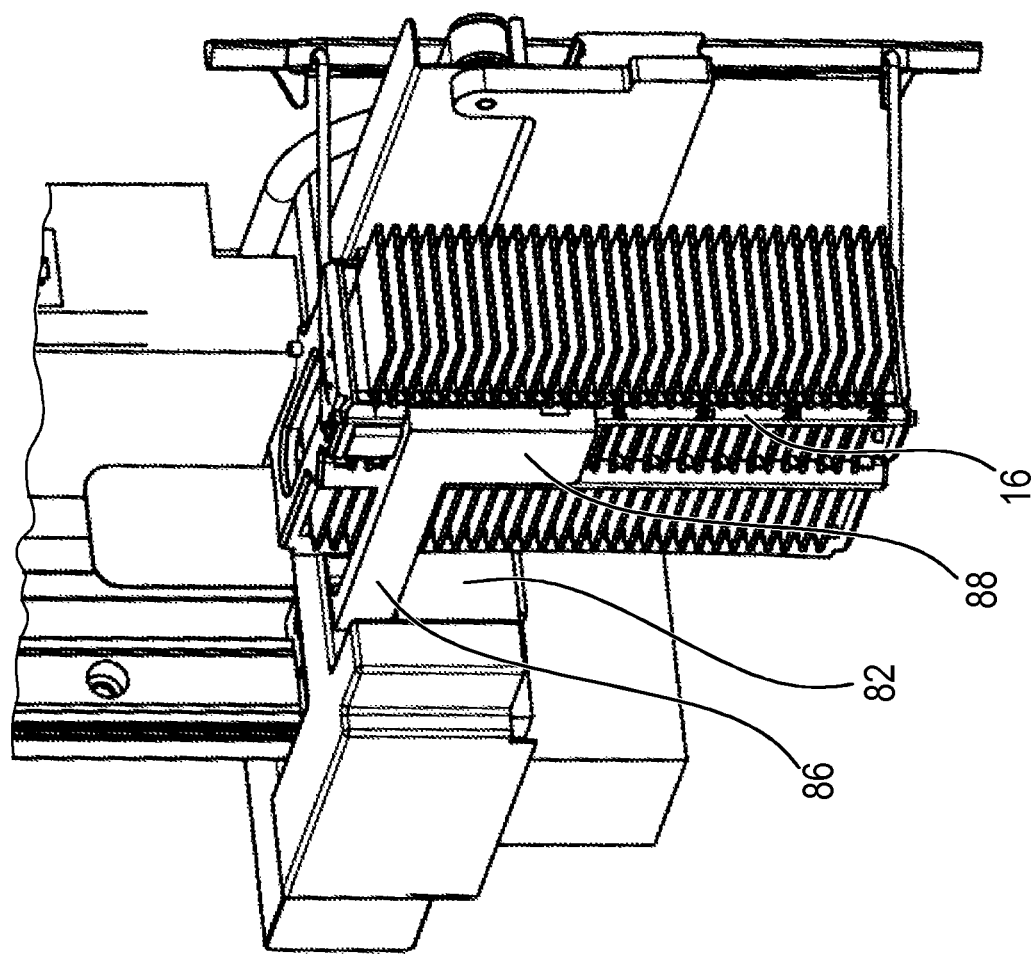
FIG. 4 is a schematic perspective view of a detail of the transport unit of FIG. 3.
Figure 5:
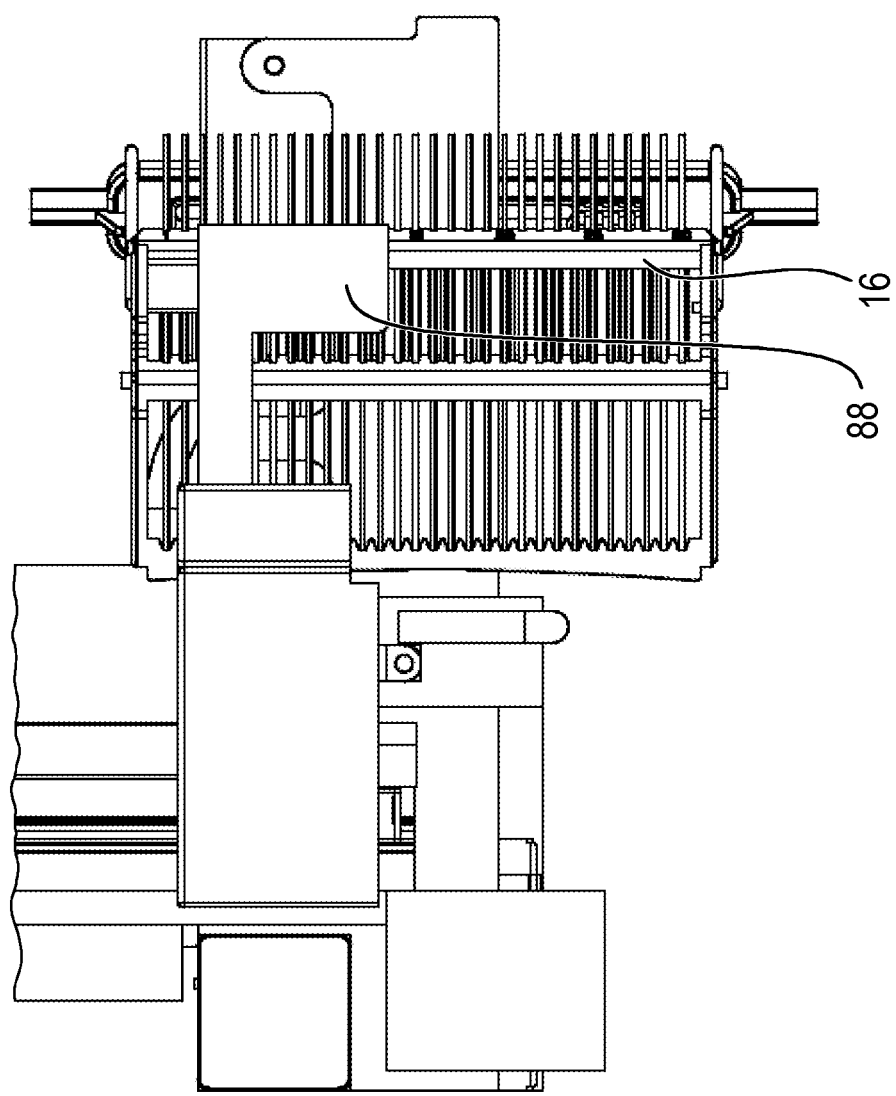
FIG. 5 is a side view of the detail shown in FIG. 4.
Figure 6:
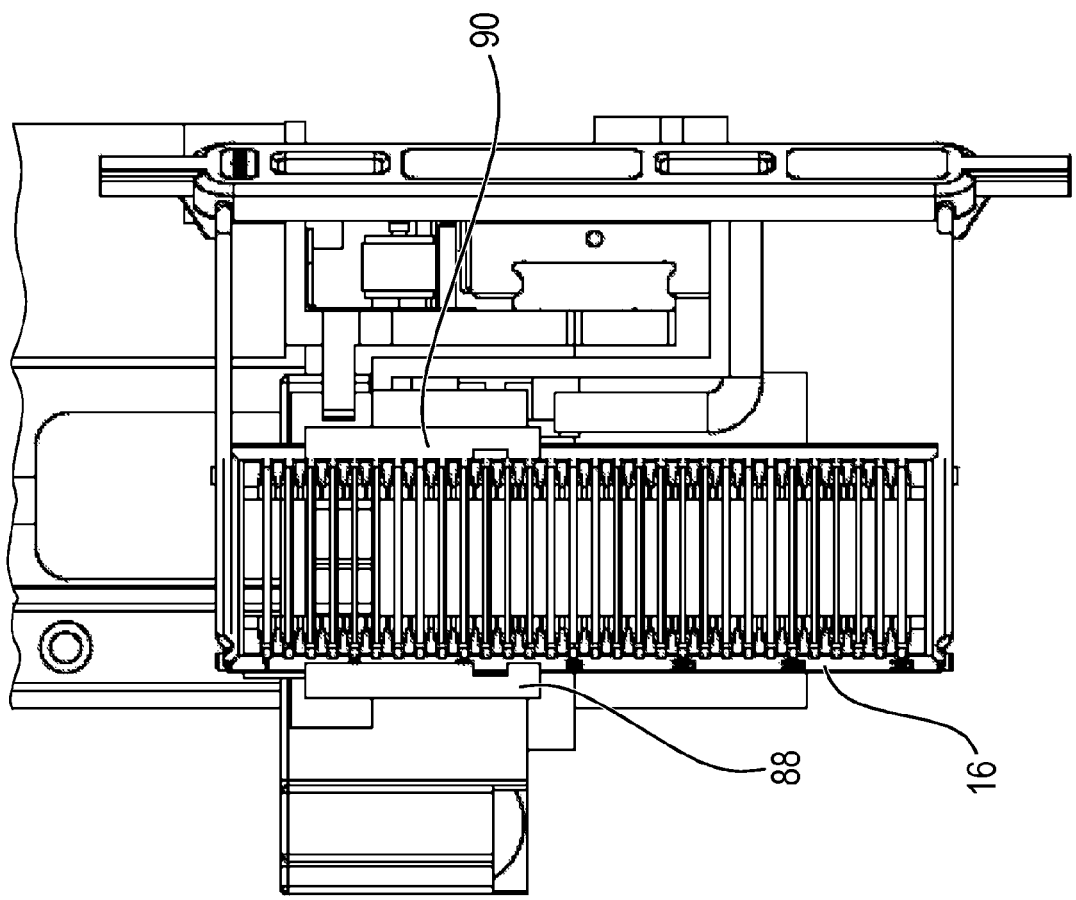
FIG. 6 is a front view of the detail shown in FIGS. 4 and 5.

Third carriage 82 has mounted thereon a gripper 86 which is used to hold the rack 16 to be transported. FIG. 4 shows a detail of transport unit 20 in a schematic perspective view, in which gripper 86 is clearly visible. FIG. 5 shows this detail in a side view, while FIG. 6 shows a front view thereof.

Gripper 86 includes a first holding member 88 and a second holding member 90 which, in a first position, are disposed such that they clamp and thus hold a rack 16 located therebetween. To this end, they are spaced apart by a first predetermined distance in a first position. In a second position, holding members 88, 90 are spaced apart by a distance greater than that in the first position, so that they no longer hold rack 16. This makes it possible to easily grip and release a rack 16.

Support unit 91, and thus first rail 68, are disposed, in particular, on a rear wall 96 of coverslipper 10, so that a compact design is achieved for transport unit 20, yet allowing it to access any desired position within a large transport space. Thus, in particular, transport unit 20 does not obstruct access to module-receiving areas 24 through 28, so that modules 30 through 34 can be easily replaced.

Rail 68 extends across nearly the entire width B of coverslipper 10, so that transport unit 20 can transport racks 16 across the entire width B of coverslipper 10. The length of second rail 70 is preferably between 0.5 and 0.7 times the height H of coverslipper 10.

Figure 7:
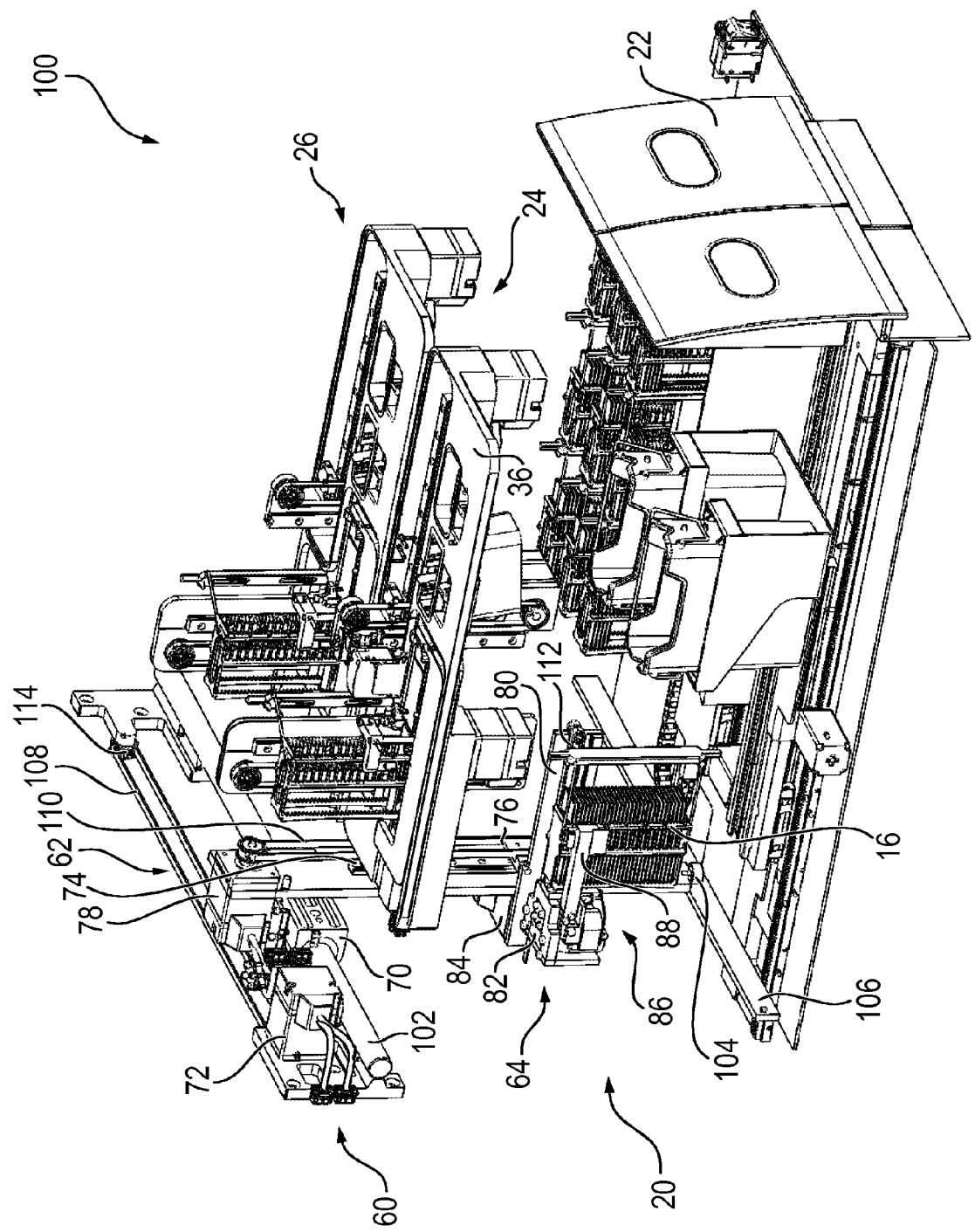
FIG. 7 is a schematic perspective view of a portion of an automated coverslipper according to a second embodiment.

FIG. 7 shows in schematic perspective form a portion of a coverslipper 100 according to a second embodiment. In this second exemplary embodiment, first linear guide 60 includes a shaft 102 instead of a rail 68 to guide carriage 70 thereon. In order to prevent tilting of carriage 70, second rail 74, which is fixedly connected to carriage 70, is supported against a rail 106 by a roller 104. Such a linear guide 60 having a shaft 102 costs less than a linear guide 60 having a rail 68.

Moreover, in the second exemplary embodiment shown in FIG. 7, belts 108 through 112, via which carriages 70, 76, 82 are moved, are disposed on the front side, so that they are visible. The belts are run over sprockets, one of which is denoted, by way of example, by reference numeral 114.

Also in the exemplary embodiment shown in FIG. 7, no modules 30, 32 are disposed in module-receiving areas 24, 26, so that support plate 36 and its cutouts are clearly visible.

In an alternative embodiment of the present invention, both or one of the two linear guides 62, 64 may include a shaft 102 instead of a rail 74, 80.

LIST OF REFERENCE NUMERALS 10 coverslipper
12 housing
14 input compartment
16 rack
18 xylene container
20 transport unit
22 output compartment
24, 26, 28 module-receiving area
30, 32 coverslipper module
34 quality control module
36 support plate
38, 40 inlet port
42 removal unit
44 hollow needle
46 suction cup device
48 cover slip
50 coverslip container
52 control unit
60, 62, 64 linear guide
68, 74, 80 rail
70, 76, 82 carriage
72, 78, 84 motor
86 gripper
88, 90 holding member
91 support unit
96 housing wall
100 coverslipper
102 shaft
104 roller
106 rail
108, 110, 112 belt
114 sprocket
P1, P2, P3 direction
B width
H height

What is claimed is:

1. A system for handling slides, comprising:
an input compartment (14) for receiving racks (16) inputted to the system, the inputted racks carrying slides to be coverslipped;
a coverslipper module (30, 32) for coverslipping thin sections on the slides with a mounting medium and a cover slip (48);
an output compartment (22) for receiving racks (16) carrying coverslipped slides, wherein the racks (16) received by the output compartment are ready to be outputted from the system;
a transport unit (20) for transporting the racks (16);
a control unit (52) for controlling the transport unit (20);
a drying unit operable to remove moisture of the mounting medium from coverslipped slides;
at least two modules (30 through 34), each module being configured for handling slides;
a first module-receiving area (24 through 28) for receiving one of the at least two modules (30 through 34); and
a second module-receiving area (24 through 28) for receiving a further one of the at least two modules (30 through 34);
wherein the transport unit (20) is operable to transport the racks (16) between the input compartment (14), the coverslipper module (30, 32) and the output compartment (22);
wherein the transport unit (20) is operable to transfer racks (16) to the drying unit and remove racks (16) from the drying unit;
wherein the transport unit (20) is operable to transfer racks (16) to a module (30 through 34) disposed in the first module-receiving area (24 through 28) and remove racks from a module (30 through 34) disposed in the first module-receiving area (24 through 28), and the transport unit (20) is operable to transfer racks (16) to a module (30 through 34) disposed in the second module-receiving area (24 through 28) and remove racks from a module (30 through 34) disposed in the second module-receiving area (24 through 28); and
wherein the at least two modules comprises the coverslipper module.

2. A system for handling slides, comprising:
an input compartment (14) for receiving racks (16) inputted to the system, the inputted racks carrying slides to be coverslipped;
a coverslipper module (30, 32) for coverslipping thin sections on the slides with a mounting medium and a cover slip (48);
an output compartment (22) for receiving racks (16) carrying coverslipped slides, wherein the racks (16) received by the output compartment are ready to be outputted from the system;
a transport unit (20) for transporting the racks (16);
a control unit (52) for controlling the transport unit (20);
a drying unit operable to remove moisture of the mounting medium from coverslipped slides;
at least two modules (30 through 34), each module being configured for handling slides;
a first module-receiving area (24 through 28) for receiving one of the at least two modules (30 through 34); and
a second module-receiving area (24 through 28) for receiving a further one of the at least two modules (30 through 34);
wherein the transport unit (20) is operable to transport the racks (16) between the input compartment (14), the coverslipper module (30, 32) and the output compartment (22);
wherein the transport unit (20) is operable to transfer racks (16) to the drying unit and remove racks (16) from the drying unit;

wherein the transport unit (20) is operable to transfer racks (16) to a module (30 through 34) disposed in the first module-receiving area (24 through 28) and remove racks from a module (30 through 34) disposed in the first module-receiving area (24 through 28), and the transport unit (20) is operable to transfer racks (16) to a module (30 through 34) disposed in the second module-receiving area (24 through 28) and remove racks from a module (30 through 34) disposed in the second module-receiving area (24 through 28); and wherein the at least two modules comprises a quality control module (34) for checking the quality of thin sections placed on the slides and/or the coverslipping quality.

3. A system for handling slides, comprising:
an input compartment (14) for receiving racks (16) inputted to the system, the inputted racks carrying slides to be coverslipped;
a coverslipper module (30, 32) for coverslipping thin sections on the slides with a mounting medium and a cover slip (48);
an output compartment (22) for receiving racks (16) carrying coverslipped slides, wherein the racks (16) received by the output compartment are ready to be outputted from the system;
a transport unit (20) for transporting the racks (16);
a control unit (52) for controlling the transport unit (20);
a drying unit operable to remove moisture of the mounting medium from coverslipped slides;
at least two modules (30 through 34), each module being configured for handling slides;
a first module-receiving area (24 through 28) for receiving one of the at least two modules (30 through 34); and
a second module-receiving area (24 through 28) for receiving a further one of the at least two modules (30 through 34);
wherein the transport unit (20) is operable to transport the racks (16) between the input compartment (14), the coverslipper module (30, 32) and the output compartment (22);
wherein the transport unit (20) is operable to transfer racks (16) to the drying unit and remove racks (16) from the drying unit;
wherein the transport unit (20) is operable to transfer racks (16) to a module (30 through 34) disposed in the first module-receiving area (24 through 28) and remove racks from a module (30 through 34) disposed in the first module-receiving area (24 through 28), and the transport unit (20) is operable to transfer racks (16) to a module (30 through 34) disposed in the second module-receiving area (24 through 28) and remove racks from a module (30 through 34) disposed in the second module-receiving area (24 through 28); and
wherein the system (10, 100) includes a first level accommodating at least one of the input compartment (14), the drying unit, and the output compartment (22), and a second level accommodating the first and second module-receiving areas (24 through 28), and wherein the transport unit (20) is operable to transport racks (16) between the first level and the second level.

4. A system for handling slides, comprising:
an input compartment (14) for receiving racks (16) inputted to the system, the inputted racks carrying slides to be coverslipped;
a coverslipper module (30, 32) for coverslipping thin sections on the slides with a mounting medium and a cover slip (48);
an output compartment (22) for receiving racks (16) carrying coverslipped slides, wherein the racks (16) received by the output compartment are ready to be outputted from the system;
a transport unit (20) for transporting the racks (16); and
a control unit (52) for controlling the transport unit (20);
wherein the transport unit (20) is operable to transport the racks (16) between the input compartment (14), the coverslipper module (30, 32) and the output compartment (22); and wherein the transport unit (20) includes:
a first linear guide member (68, 102) oriented in a first direction (P1);
a first carriage (70) mounted on the first guide member (68, 102) to be movable in the first direction (P1) and in a direction opposite to the first direction (P1);
a second linear guide member (74) oriented in a second direction (P2) orthogonal to the first direction (P1), the second guide member (74) being disposed on and fixedly connected to the first carriage (70)
a second carriage (76) mounted on the second guide member (74) to be movable in the second direction (P2) and in a direction opposite to the second direction (P2); and
a gripper (86) operable to hold at least one rack (16) while the rack (16) is being transported, wherein the gripper is movable by the first carriage (70) in the first direction (P1) and in the direction opposite to the first direction (P1), and by the second carriage (76) in the second direction (P2) and in the direction opposite to the second direction (P2).

5. The system (10, 100) as recited in claim 4, wherein each of the first guide member (68, 102), the second guide member (74), and the third guide member (80) is configured as a shaft or as a rail.

6. The system (10, 100) as recited in claim 4,
wherein the gripper (86) includes a first holding member (88) and a second holding member (90) for holding the rack (16) to be transported;
in a first position, the holding members (88, 90) are spaced apart by a first predetermined distance at which the holding members (88, 90) hold a rack (16) located therebetween;
in a second position, the holding members (88, 90) are spaced apart by a second predetermined distance at which the holding members (88, 90) do not hold a rack (16) located therebetween; and
the gripper includes at least one elastic member urging the holding members (88, 90) into the first position.

7. The system (10, 100) as recited in claim 4, wherein the gripper (86) includes at least one engagement element arranged to engage a complementary engagement element of a rack (16) so as to hold the rack (16).

8. The system (10, 100) as recited in claim 4, comprising:
a first drive motor (72);
a first belt (108) connected to the first carriage (70) and driven by the first drive motor (72) to move the first carriage (70) along the first guide member (68, 102);
a second drive motor (78); and
a second belt (110) connected to the second carriage (76) and driven by the second drive motor (78) to move the second carriage (76) along the second guide member (74).

9. The system (10, 100) as recited in claim 8, comprising:
a housing (12) enclosing the input compartment (14), the coverslipper module (30, 32), the output compartment (22), the transport unit (20) and the control unit (52), the housing having a wall (96);

wherein the first guide member (68, 102) is mounted on the wall (96) of the housing (12).

10. The system (10, 100) as recited in claim 8, comprising:
a third linear guide member (80) oriented in a third direction (P3) orthogonal to the first direction (P1) and orthogonal to the second direction (P2), the third guide member (80) being disposed on and fixedly connected to the second carriage (76);
wherein the gripper (86) is mounted on the third guide member (74) to be movable in the third direction (P3) and in a direction opposite to the third direction (P3).

11. The system (10, 100) as recited in claim 10, comprising
a third drive motor (84); and
a third belt (112) connected to the gripper (86) and driven by the third drive motor (72) to move the gripper (86) along the third guide member (80).

12. The system (10, 100) as recited in claim 8, comprising:
a housing (12) enclosing the input compartment (14), the coverslipper module (30, 32), the output compartment (22), the transport unit (20) and the control unit (52), the housing having a width (B) and a height (H);
wherein the length of the first guide member (68, 102) is between 0.8 and 0.95 times the width (B) of the housing (12).

13. The system (10, 100) as recited in claim 12, wherein the length of the second guide member (74) is between 0.5 and 0.95 times the height (H) of the housing (12).

14. The system (10, 100) as recited in claim 13, wherein the length of the second guide member (74) is between 0.6 and 0.7 times the height (H) of the housing (12).

* * * * *